United States Patent
Langer et al.

(10) Patent No.: US 12,303,659 B2
(45) Date of Patent: May 20, 2025

(54) THERMALLY CONTROLLED RECONFIGURABLE MEDICAL DEVICES

(71) Applicants: Massachusetts Institute of Technology, Cambridge, MA (US); The Brigham and Women's Hospital, Inc., Boston, MA (US)

(72) Inventors: Robert S. Langer, Newton, MA (US); Carlo Giovanni Traverso, Newton, MA (US); Sahab Babaee, Arlington, MA (US); Simo Pajovic, Mississauga (CA); Ester Caffarel Salvador, Cambridge, MA (US)

(73) Assignees: Massachusetts Institute of Technology, Cambridge, MA (US); The Brigham and Women's Hospital, Inc., Boston, MA (US)

( * ) Notice: Subject to any disclaimer, the term of this patent is extended or adjusted under 35 U.S.C. 154(b) by 905 days.

(21) Appl. No.: 17/293,804

(22) PCT Filed: Nov. 15, 2019

(86) PCT No.: PCT/US2019/061667
§ 371 (c)(1),
(2) Date: May 13, 2021

(87) PCT Pub. No.: WO2020/102650
PCT Pub. Date: May 22, 2020

(65) Prior Publication Data
US 2022/0023602 A1    Jan. 27, 2022

Related U.S. Application Data

(60) Provisional application No. 62/767,798, filed on Nov. 15, 2018, provisional application No. 62/767,954, filed on Nov. 15, 2018.

(51) Int. Cl.
A61M 31/00    (2006.01)
A61M 37/00    (2006.01)

(52) U.S. Cl.
CPC .......... A61M 31/002 (2013.01); A61M 37/00 (2013.01); A61M 2205/0266 (2013.01); A61M 2210/105 (2013.01)

(58) Field of Classification Search
CPC ................ A61M 31/002; A61M 37/00; A61M 2205/0266; A61M 2210/105;
(Continued)

(56) References Cited

U.S. PATENT DOCUMENTS 6,077,298 A    6/2000  Tu et al.
2003/0109897 A1    6/2003  Walak et al.
(Continued)

OTHER PUBLICATIONS

International Search Report and Written Opinion for PCT/US2019/061667 mailed Jan. 14, 2020.
(Continued)

*Primary Examiner* — Jessica Arble
*Assistant Examiner* — Nhu Q. Tran
(74) *Attorney, Agent, or Firm* — Wolf, Greenfield & Sacks, P.C.

(57) ABSTRACT

Systems and methods related to reconfigurable medical devices are described. In some embodiments, a reconfigurable medical device may include a central core and a plurality of arms. The arms may be rotatably coupled to the central core such that the plurality of arms may rotate outwards away from the central core to selectively reconfigure the reconfigurable device between a retracted configuration and an expanded configuration. In an initial state, the arms may be biased outwards away from the central core into the expanded configuration. When the reconfigurable device is exposed to a temperature greater than a threshold temperature, the arms may be biased towards the central
(Continued)

core into the retracted configuration. In some embodiments, a reconfigurable medical device may include therapeutic compound-loaded needles coupled to distal portions of the arms.

12 Claims, 8 Drawing Sheets

(58) Field of Classification Search
CPC .......... A61M 2210/1042; A61M 25/04; A61M 25/0067; A61M 25/0074; A61M 2025/0096
See application file for complete search history.

(56) References Cited

U.S. PATENT DOCUMENTS

| | | |
|---|---|---|
| 2005/0234503 A1 | 10/2005 | Ravenscroft et al. |
| 2005/0277964 A1 | 12/2005 | Brenneman et al. |
| 2009/0182303 A1* | 7/2009 | Walak ................... A61F 5/0013 514/10.8 |
| 2010/0318115 A1* | 12/2010 | Chanduszko ......... A61F 2/0105 606/200 |
| 2014/0276408 A1* | 9/2014 | Abbate ................... A61F 2/186 606/198 |
| 2015/0342877 A1* | 12/2015 | Menachem ......... A61M 31/002 604/890.1 |
| 2017/0079679 A1* | 3/2017 | Pigott ............... A61M 25/0074 |
| 2017/0106099 A1 | 4/2017 | Bellinger et al. |
| 2020/0008920 A1* | 1/2020 | Park ................... A61B 17/3468 |
| 2020/0030589 A1* | 1/2020 | Ben Menachem .. A61B 5/6871 |
| 2021/0275795 A1* | 9/2021 | Agah ................... A61M 60/165 |
| 2022/0008701 A1 | 1/2022 | Langer et al. |

OTHER PUBLICATIONS

International Preliminary Report on Patentability for PCT/US2019/061667 mailed May 27, 2021.

Babaee et al., Temperature-responsive biometamaterials for gastrointestinal applications. Science Translational Medicine. Apr. 17, 2019;11(488):13 pages. Supplementary Materials included. 26 pages total.

U.S. Appl. No. 17/293,799, filed May 13, 2021, Langer et al.

* cited by examiner

THERMALLY CONTROLLED RECONFIGURABLE MEDICAL DEVICES

CROSS-REFERENCE TO RELATED APPLICATIONS

This application is a national stage filing under 35 U.S.C. § 371 of International application serial number PCT/US2019/061667, filed Nov. 15, 2019, which claims the benefit under 35 U.S.C. § 119 (e) of U.S. provisional application Ser. No. 62/767,954, filed Nov. 15, 2018, and 62/767,798, filed Nov. 15, 2018, the disclosures of which are incorporated by reference in their entirety.

GOVERNMENT LICENSE RIGHTS

This invention was made with Government support under Grant No. R37 EB000244 awarded by the National Institutes of Health. The Government has certain rights in the invention.

FIELD

Disclosed embodiments are related to thermally controlled reconfigurable medical devices.

BACKGROUND

Medical devices designed for use in the gastrointestinal (GI) tract have been applied broadly across clinical indications ranging from cancer (stents, percutaneous gastrostomy tubes), bariatrics (balloons), and systems for drug delivery and long-term energy harvesting. However, previous approaches have often been constrained by slow response times, which may pose a major limitation for many potential applications.

SUMMARY

In one embodiment, a reconfigurable medical device includes a central core and a plurality of arms rotatably coupled to the central core. The plurality of arms may be configured to rotate outwards away from the central core to selectively reconfigure the reconfigurable device between a first retracted configuration and a second expanded configuration. In an initial state the plurality of arms are biased outwards away from the central core into the second expanded configuration, and when the reconfigurable device is exposed to a temperature greater than a threshold temperature the plurality of arms are may be biased towards the central core into the first retracted configuration.

In another embodiment, a method of reconfiguring the shape of a reconfigurable medical device includes: biasing a plurality of arms outward away from a central core of the reconfigurable medical device to reconfigure the reconfigurable medical device from a first retracted configuration to a second expanded configuration; and exposing the reconfigurable medical device to a temperature greater than a threshold temperature to bias the arms towards the central core to reconfigure the reconfigurable medical device from the second expanded configuration to the first retracted configuration.

In yet another embodiment, a method of delivering a therapeutic compound includes: positioning a reconfigurable medical device in a retracted configuration in an anatomical structure of a subject; deploying a plurality of arms of the reconfigurable medical device using stored elastic energy to retain the reconfigurable medical device in the anatomical structure; and delivering the therapeutic compound to tissue of the anatomical structure.

In still another embodiment, an apparatus includes a radially expandable structure including a plurality of needles extending outward from the structure. The needles may be loaded with a therapeutic compound. Further, the needles may be configured to deliver the therapeutic compound to mucosal tissue of an esophagus of a subject when the radially expandable structure is in an expanded configuration.

In another embodiment, a method of delivering a therapeutic compound includes: radially deploying a plurality of needles into mucosal tissue of an esophagus of a subject; and delivering a therapeutic compound from the needles into the mucosal tissue.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. In the drawings.

DETAILED DESCRIPTION

Figure 1A:
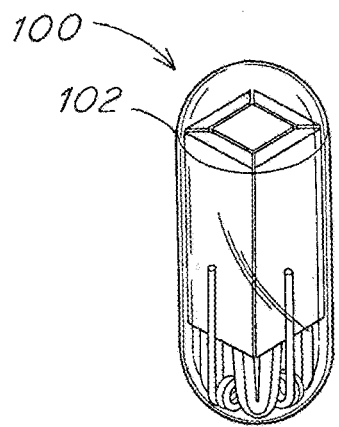
FIG. 1A depicts one embodiment of a reconfigurable medical device in a retracted configuration within a capsule.

The inventors have recognized that conventional gastrointestinal (GI) devices with triggerable control may be restricted to a slow response. Specifically, these devices often exploit light, pH, magnetic and solvent responsive materials for actuation. The Inventors have recognized and appreciated that using temperature-sensitive components may enable a new generation of medical devices configured to respond quickly to applied temperature changes.

In some embodiments, a reconfigurable medical device may comprise a temperature-triggered bi-stable device. The device may include a central core and multiple arms attached to and configured to rotate relative to the central core. In some embodiments, distal portions of the arms may be equipped with needles configured to deliver therapeutic compounds to the esophagus, or other structure, without perforation. However, embodiments without needles are also envisioned. The device may be able to fold into a retracted form that can be easily delivered to the esophagus or other anatomical structure in any appropriate manner. Upon reaching the esophagus, or other desired location within a subject's body, the device may be permitted to transform from the retracted configuration into an expanded configuration in which the arms of the device may pivot away from the central body, resulting in penetration of the needles into the esophageal mucosa and delivery of therapeutic compound to the esophageal mucosa. The device may retract to its original shape through the activation of thermo-responsive components, such as a shape-memory material, that may be triggered via a temperature change. The desired temperature change may be applied in any desired manner as elaborated on below. Upon triggering, the device may reconfigure from the expanded configuration with a larger transverse dimension (e.g. a width or diameter) to the retracted configuration with a smaller transverse dimension to enable the device to subsequently pass through the gastrointestinal tract or to otherwise be removed from the esophagus or other anatomical structure.

In one embodiment, a reconfigurable medical device may include a central core and multiple arms that are rotatably coupled to a central core. In some embodiments, the arms may be biased away from the central core via one or more flexible elastic components. Depending on the particular embodiment, a flexible elastic component may be attached to and extend between an associated arm and the central core and/or between adjacent arms. In either case, elastic energy stored in a flexible elastic component when the device is in a retracted configuration may apply a force to the associated arms to bias the device from the retracted configuration to the expanded configuration during deployment. Thus, the arms may be biased radially outward from the body by the associated flexible elastic components. While the use of flexible elastic beams is described in relation to the figures, other appropriate flexible elastic components that may be used include but are not limited to springs (such as torsion springs) connected between an arm and central core, elastic living hinges disposed between an arm and central core, and/or any other flexible elastic structure configured to bias the arms away from the central core. Accordingly, it should be understood that various components and configurations may be used to apply the desired deployment forces to a device.

In some embodiments, a reconfigurable medical device may also include one or more thermo-responsive components. Upon heating to a threshold temperature, the thermo-responsive components may apply a force to the arms to bias the arms towards a central core of the device such that the device is biased from the expanded configuration to the retracted configuration. The force applied by the thermo-responsive components may be sufficient to overcome a force applied by the elastic beams, or other elastic component, that is applied in an opposing direction to apply an overall force that biases the device into the retracted configuration. In some embodiments, the thermo-responsive components may apply a force to the arms to bias the device from the expanded configuration to the retracted configuration when the device is in the expanded configuration without heating. For example, deformation of the thermo-responsive components may result in a restoring force that biases the arms towards the core. However, the force applied by the thermo-responsive components without heating may be less than a force applied by the elastic components biasing the arms away from the core, such that the device remains in the expanded configuration. That is, in some embodiments, there may be competing forces exerted by the elastic beams (or other elastic component) and the thermo-responsive components. However, when exposed to a temperature greater than a threshold temperature, the force applied to an associated arm by a thermo-responsive component biasing the arm towards the retracted configuration may be greater than the opposing force applied to the arm by the associated elastic component. Thus, the device may be biased toward the retracted configuration by increasing the temperature of the thermo-responsive components to be greater than the threshold temperature. This may correspondingly cause an overall force applied to the arms to be directed towards the core to bias the device into the retracted configuration.

While the use of a reconfigurable medical device in the esophagus of a subject is described above, it should be understood that the current disclosure is not limited to using temperature triggered reconfigurable medical devices only in the esophagus and/or gastrointestinal tract of a subject. For example, the disclosed medical devices may be used in any appropriate anatomical structure in the body where it may be desirable to have a device transition between an expanded configuration and a retracted configuration for delivery of a therapeutic compound and/or sensing applications. Other appropriate types of anatomical structures where the disclosed medical devices may be used include, but are not limited to, a small intestine, large intestine, trachea, colon, ureters, urethra, and any tubular viscus of a subject.

In some embodiments, a reconfigurable medical device may be deployed in a body of a subject through ingestion. For example, a device may be enclosed within a capsule, such as a gelatin or other dissolvable capsule, in the retracted configuration. A subject may swallow the encapsulated device, introducing the device into the gastrointestinal tract. The capsule may be configured to dissolve after a predetermined time or upon reaching a predetermined environment, allowing the device to be deployed at a predetermined location within the body of the subject. However, in some embodiments, the device may be deployed in the body endoscopically, surgically, or in any other appropriate manner, as the disclosure is not limited in regards to the method of deploying the device to a desired location within a subject's body.

As noted above, a temperature change may be applied to a reconfigurable medical device in any appropriate manner. For example, in one embodiment, a warm liquid, such as water, may be ingested. Alternatively, a warm liquid may be sprayed or otherwise applied to the device using an endoscopic or other delivery device. In another embodiment, one or more components of a device may be made from a conductive material such that the device is capable of interacting with an applied varying electromagnetic field to enable radiofrequency heating (RF heating) using a radiofrequency source located outside of a subject. In view of the foregoing, it should be understood that the disclosed devices may be heated using surgical applied heating sources, ingested heating sources, externally applied heating sources, and/or any other appropriate heat source, as the disclosure is not limited in this fashion.

As described below, experiments were conducted in a large animal model that assisted in understanding anatomical, temporal and thermal boundary conditions in the upper gastrointestinal tract obtained upon ingestion of warm liquids. Accordingly, in some embodiments, the actuation temperature threshold to cause a medical device to transition between different configurations may be greater than normothermia within a desired anatomical structure, such as the esophagus, in which the device is deployed. For example, normothermia within the esophagus is approximately 37° C. Thus, a threshold temperature for thermal actuation of a device may be greater than or equal to 40° C., 45° C., 50° C., and/or any other appropriate temperature. Correspondingly, the threshold temperature may be less than or equal to 65° C., 60° C., 55° C., 50° C., and/or any other appropriate temperature. Combinations of the foregoing are contemplated including a threshold temperature that is between or equal to 40° C. and 65° C. Of course it should be understood that depending on the particular application, threshold temperatures both greater and less than those noted above are also contemplated as the disclosure is not limited in this fashion.

It should be understood that the various components of a reconfigurable medical device may be made from any appropriate material compatible with the anatomical structures with which the device will interact during use and exhibiting appropriate properties for a desired application. In some embodiments, the arms and the central core may be made from a suitable material and may have appropriate dimensions to provide a desired rigidity during deployment and use. Appropriate materials may include, but are not limited to: polymeric materials such as poly(ε-caprolactone) (PCL), thermoplastic polyurethanes (TPUs), poly(vinyl alcohol) (PVA), polylactic acid (PLA), poly(lactic-co-glycolic acid) (PLGA), silicone-based elastomers with high shore hardness, metals, and/or any other appropriate material.

An elastic component may be made from any sufficiently elastic material and may have any appropriate construction to provide a desired biasing force to bias a reconfigurable medical device to an expanded configuration. Appropriate materials may include, but are not limited to: elastic and/or elastomeric polymers such as thermoplastic polyurethane, silicon-based elastomers, polydimethylsiloxane (PDMS), and other appropriate polymers; flexible metals such as stainless steel, titanium, alloys thereof, and other metals compatible with the anatomical structure with which the device may interact; and/or any other appropriate elastic material. Depending on the specific material and corresponding elasticity, the elastic components may take any number of different forms including, but not limited to, springs, beams, solid components, components with portions having reduced cross sections to form living hinges, and/or any other appropriate structure exhibiting a desired combination of flexibility and stiffness to provide the desired functionality.

As noted above, a reconfigurable medical device may use a thermo-responsive component that biases the reconfigurable medical device to a retracted configuration upon the application of a temperature change. In some embodiments, the device may include springs made of a shape memory material that may apply a force biasing the arms toward a core of the device when the device is exposed to an elevated temperature above a threshold temperature. For example, in some embodiments, a reconfigurable medical device may include shape memory springs to enable the temperature based triggering and closure of the device (i.e., transformation from the expanded configuration to the retracted configuration). While a spring is noted above, in some embodiments, the thermo-responsive component may include other appropriately shaped components capable of applying a desired force. For example, by selecting an appropriate constructions may include a U-shaped structure, an L-shaped structure, or any other suitably shaped structure extending between the core of a device and an associated arm. Further the various parameters of the component including material properties, dimensions, overall geometry, and other appropriate parameters may be selected to provide a desired restoring force upon thermal activation. Accordingly, it should be understood that a thermo-responsive component is not limited to only the specific structures described herein.

In some embodiments, a shape memory material may be a shape memory alloy, such as nickel-titanium (Nitinol) alloy, or other biocompatible shape memory alloy suitable for biomedical applications. In other embodiments, the shape memory material may be a shape memory polymer. For example, a shape memory polymer may include shape memory polyurethane, polyethylene terephthalate, or polyethyleneoxide, although other shape memory polymers are contemplated and the disclosure is not limited in this regard.

Without wishing to be bound by theory, a shape memory material may undergo a transformation upon heating above a transition temperature ($T_a$). That is, the shape memory material may exhibit a first configuration below the transition temperature, and may exhibit a second configuration above the transition temperature. These different configurations of the shape memory material may be exploited to apply different forces at different temperatures. Thus, the force exerted by a thermo-responsive component, such as shape memory springs, beams, or other components may be controlled through an initial setting heat treatment to set a desired configuration of a thermo-responsive component. Thus, when deformed from this initial desired configuration and exposed to temperatures greater than a threshold temperature (i.e. the transition temperature of the material), the thermal-responsive component may experience a restoring force that biases the component back towards the retained shape that was previously set. For example, shape memory springs may exhibit greater recoiling forces towards an initial undeformed configuration upon triggering at temperatures above the transition temperature.

In some applications, it may be desirable to be able to quickly reconfigure a medical device. Actuation time of the device may refer to the amount of time for the device to reconfigure from the expanded configuration to the retracted configuration through thermal activation of a component of the device. In some embodiments, the actuation time of the shape memory components of a device may be less than 10 minutes, 5 minutes, 1 minute, 10 seconds, and/or any other appropriate time period. Additionally, in some embodiments, the above-noted actuation times may be greater than 0.5 seconds, 1 second, and/or any other appropriate time period. Combinations of the foregoing are contemplated including, for example, actuation times that are between or equal to 0.5 seconds and 1 minute, 0.5 seconds and 10 minutes, and/or any other appropriate time period including time periods both greater and less than those noted above.

Therapeutic compounds for purposes of this application may correspond to any appropriate material including, but not limited to, any drug, medication, pharmaceutical preparation, contrast agent, and/or biologic such as a protein, antisense molecule, and gene therapy viral vector as the disclosure is not so limited. When a therapeutic compound is present in a particular location in an "effective amount" it means a concentration of the therapeutic compound is greater than or equal to a trace amount and is sufficient for achieving a desired purpose, such as, for example, to permit detection of the therapeutic compound in a subject for diagnostic purposes, to treat a disease or condition in a subject, and/or enhance a treatment of a disease or condition in a subject. In some embodiments, an effective amount of a particular therapeutic compound is present in an amount sufficient to reduce or alleviate one or more conditions associated with a particular condition.

In addition to the above, while various embodiments of a reconfigurable medical device are described as having needles loaded with a therapeutic compound, embodiments in which different tools and/or structures are used with the disclosed reconfigurable medical devices are also contemplated. For example, a biopsy tool such as a biopsy needle or biopsy gripper, for collecting a tissue biopsy may be included on a distal portion of the arms of a device in place of the disclosed needles. In such an embodiment, a biopsy tool may collect a biopsy sample when the arms are expanded within an anatomical structure deploying the biopsy tool against tissue of the anatomical structure to collect the sample. Alternatively, one or more sensors may be included in the core or attached to one or more of the arms for sensing one or more relevant biological parameters of the subject when a reconfigurable medical device is held in place within an anatomical structure as described herein while measurements are taken. Accordingly, it should be understood that the various embodiments of a reconfigurable medical device described herein may include any number of different components to provide any number of different functionalities as the disclosure is not limited in this fashion.

Turning to the figures, specific non-limiting embodiments are described in further detail. It should be understood that the various systems, components, features, and methods described relative to these embodiments may be used either individually and/or in any desired combination as the disclosure is not limited to only the specific embodiments described herein.

Figure 1B:
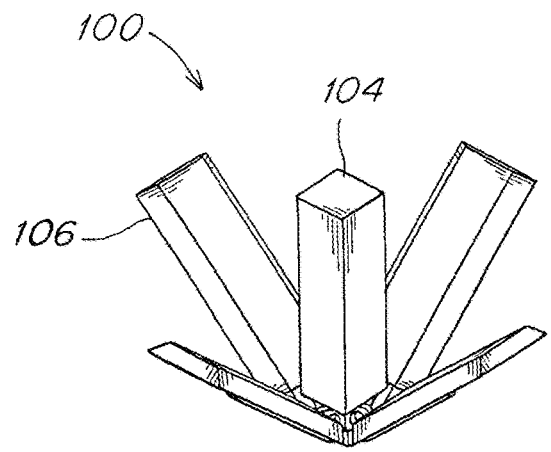
FIG. 1B depicts the reconfigurable medical device shown in FIG. 1A in a partially expanded configuration.
Figure 1C:
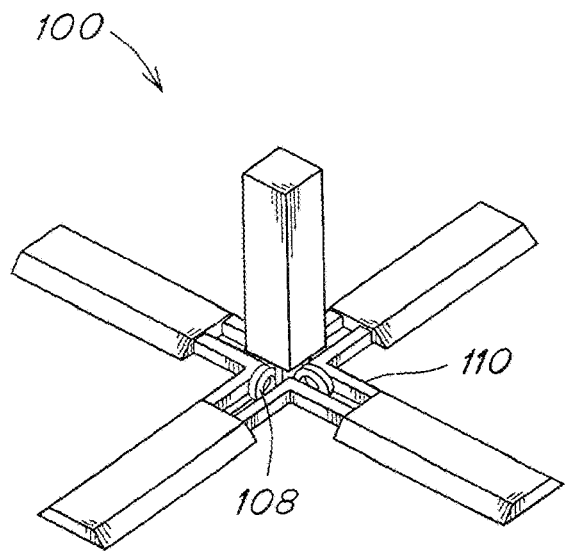
FIG. 1C depicts the reconfigurable medical device shown in FIG. 1A in a fully expanded configuration.

FIGS. 1A-1C depict one embodiment of a reconfigurable medical device 100 in various configurations. FIG. 1A shows the device in a retracted configuration within a capsule 102. FIG. 1B shows the device in a partially expanded configuration, while FIG. 1C shows the device in a fully expanded configuration.

In some embodiments, a reconfigurable medical device 100 may include a central core 104 and a plurality of arms 106. The arms 106 may be coupled to one another with one or more elastic components, such as beams 110. Thermoresponsive components, such as springs 108, may couple the arms to the central core. Specifically, as shown in the figures, the beams may have a L shape, or other angled shape, such that the straight portions of the beam are aligned with and extend along at least a portion of a length of adjacent arms. The beams, or other elastic component, may be attached to the arms using any appropriate method including adhesives, welding, mechanical interlocking features, interference fits and/or any other appropriate attachment method. The springs are torsional springs which including one or more coils with the opposing ends attached to the core and a corresponding arm as shown in the figure. The spring, or other thermo-responsive component, may be attached to the core and arms using any appropriate attachment method similar to those noted above for the elastic component. A capsule 102, such as a dissolvable gelatin capsule, may at least partially surround the central core and the arms, retaining the arms in the retracted configuration prior to deployment. In this configuration, the L-shaped beams may be deformed such that elastic energy is stored in the structure and a biasing force is applied to the arms that biases the arms towards an expanded configuration as elaborated on below. While the elastic components and thermo-responsive elements are shown in the drawings as L-shaped beams and springs (respectively), it should be appreciated that any suitable geometries and/or structures may be used for the elastic components and the thermo-responsive components as the disclosure is not limited in this regard.

The arms may be rotatably coupled to the central core in any appropriate manner that permits the arms to pivot outward away from the central core to selectively reconfigure the reconfigurable device between a retracted configuration and an expanded configuration. In some instances, the arms may rotate about an axis of rotation that is approximately perpendicular to a direction of a longitudinal axis of the central core. In some embodiments, beams 110 may be L-shaped beams that may couple two adjacent arms, such that each arm may be perpendicular to its two adjacent arms. When the arms are brought into the retracted configuration, the L-shaped beams may be deformed relative to their undeformed neutral configuration. Thus, in a retracted configuration, the arms may be biased outwards away from the central core into the expanded configuration by the L-shaped beams or other elastic component. For example, a capsule 102 may retain the device in a retracted configuration (FIG. 1A). In such a configuration, beams 110 may be deformed, storing elastic energy. When the capsule is removed (e.g., when a gelatin capsule is dissolved in the esophagus), the stored elastic energy of the beams may cause the arms to unfold (FIG. 1B), causing the device to expand. In a fully expanded configuration (FIG. 1C), the arms may be substantially perpendicular to the long axis of the central core.

In the expanded configuration, one or more thermo-responsive components associated with each arm, i.e. thermo-responsive springs 108, may exert a torque on the arms 106 to urge the arms back towards the central core 104. A spring 108 may be coupled to the central core 104 on one side and to an arm 106 on an opposite side. The spring may be operatively coupled to the arm and/or the core through the use of an adhesive, an interference fit with a hole, simply being placed into contact with the arm with a portion of the arm disposed between the L-shaped beam or other elastic component and the spring, or any other suitable method of associating the thermo-responsive component with the corresponding arm. Using such a configuration, when the springs, or other thermo-responsive components, are below a threshold temperature, such as a transition temperature of a shape memory material, the torque exerted on the arms by the springs (which may bias the arms towards the central core) may be less than the torque exerted on the arms by the beams 110 (which may bias the arms away from the core). As such, the device 100 may remain in an expanded configuration when the springs are below the threshold temperature. In contrast, when the reconfigurable device 100 is exposed to a temperature greater than a threshold temperature, the plurality of arms 106 may become biased towards the central core 104 into the retracted configuration. Specifically, the torque exerted on the arms 106 by the springs 108 (which may bias the arms towards the central core) may be greater than the torque exerted on the arms 106 by the beams 110 (which may bias the arms away from the core), which may cause the arms to retract towards the central core.

In some embodiments, the arms 106 may be biased towards the central core 104 by springs 108. As elaborated on below, the springs may be made from a shape memory material, such as a shape memory alloy or a shape memory polymer. Upon thermal activation, the springs may retract the arms to reconfigure the device into the retracted configuration. As described above, thermal activation may be accomplished by exposing the device to a temperature greater than a threshold temperature, such as the transition temperature of a shape memory material. The device may be heated through contact with a warm liquid, such as a warm liquid ingested through the mouth of a subject though other methods of applying a temperature change are also contemplated as described previously.

FIGS. 2A-2D depict various components of a reconfigurable medical device. In some embodiments of a reconfigurable medical device, not all of the components shown in FIGS. 2A-2D may be included. In some embodiments of a reconfigurable medical device, additional components beyond the components shown in FIGS. 2A-2D may be included.

Figure 2A:
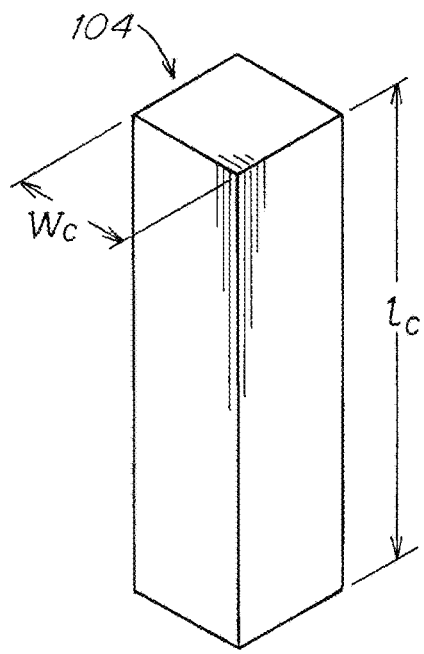
FIG. 2A depicts one embodiment of a central core of a reconfigurable medical device.

FIG. 2A depicts one embodiment of a central core 104. In some embodiments, the central core may be made of plastic, such as a thermoplastic. In some embodiments, the central core may be made of a thermoplastic polyester, such as poly(ε-caprolactone) (PCL). Of course, other suitable materials may be used to make the central core, as the disclosure is not limited in this regard. The central core may have a length $l_c$ and a width $w_c$. In some embodiments, the length of the core may be less than 100 mm, 50 mm, 30 mm, 20 mm, or 10 mm. In some embodiments, the length of the core may be greater than 1 mm, 5 mm, 10 mm, 20 mm, or 50 mm. In some embodiments, the length of the core may be approximately 15 mm. In some embodiments, the width of the core may be less than 20 mm, 10 mm, 5 mm, 2 mm or 1 mm. In some embodiments, the width of the core may be greater than 0.5 mm, 1 mm, 5 mm, or 10 mm. In some embodiments, the width of the core may be approximately 3.8 mm. Of course, other suitable materials, geometries, and dimensions are possible as the disclosure is not limited in this regard.

Figure 2B:
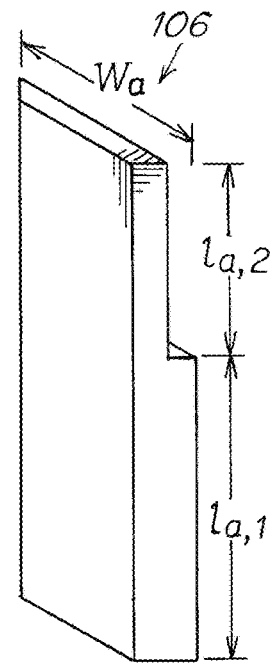
FIG. 2B depicts one embodiment of an arm of a reconfigurable medical device.

FIG. 2B depicts one embodiment of an arm 106. The arm may be made of the same material as the central core 104, or may be made of a different material. The arm may have a length $l_a$ and a width $w_a$. The length $l_a$ may be composed of a proximal length $l_{a,1}$ and distal length $l_{a,2}$. In some embodiments, the distal length $l_{a,2}$ may be associated with a geometry configured to accept another component of a reconfigurable medical device. For example, the distal length of the arm may be associated with a recess or a flat configured to mate with a needle base of a needle loaded with a therapeutic compound. In some embodiments, the width of the arm may be less than 15 mm, 10 mm, 5 mm, 2 mm, or 1 mm. In some embodiments, the width of the arm may be greater than 0.1 mm, 0.5 mm, 1 mm, 2 mm, or 5 mm. In some embodiments, the width of the arm may be approximately 6 mm. In some embodiments, the length of the arm may be less than 100 mm, 50 mm, 30 mm, 20 mm, or 10 mm. In some embodiments, the length of the arm may be greater than 1 mm, 5 mm, 10 mm, 20 mm, or 50 mm. In some embodiments, the length of the arm may be approximately 15 mm. Of course, other suitable materials, geometries, and dimensions, including dimensions both greater and less than those noted above, are possible as the disclosure is not limited in this regard.

Figure 2C:
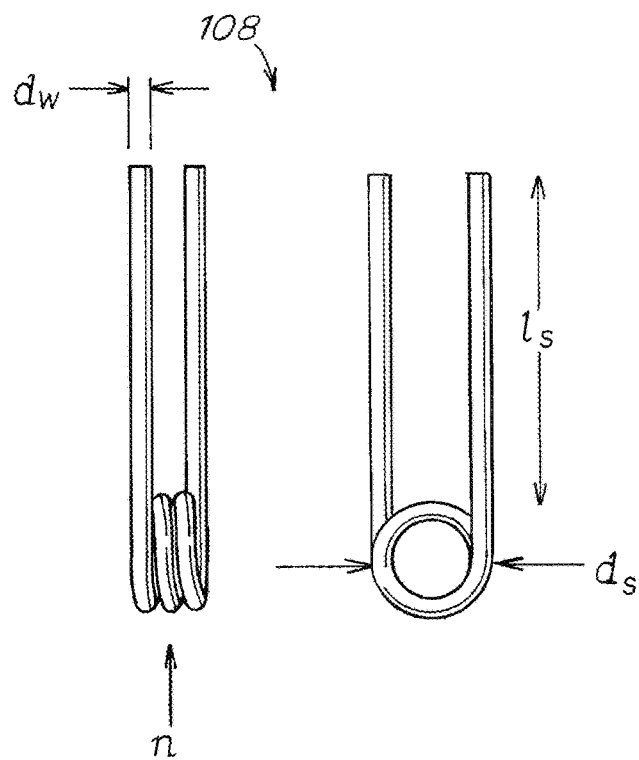
FIG. 2C depicts one embodiment of a spring of a reconfigurable medical device.

FIG. 2C depicts one embodiment of a spring 108. In some embodiments, a spring may be a shape memory material. For example, a spring may be a shape memory alloy, such as nickel-titanium (Nitinol), or a shape memory polymer. Other suitable temperature-responsive materials may be used in spring 108, as the disclosure is not limited in this regard. The spring may have an arm length $l_s$, a coil diameter $d_s$, and a wire diameter $d_w$. The spring may include n coils. As described above, the geometry and material of a shape memory spring may affect the transition temperature of the shape memory spring. In some embodiments, a wire may have a diameter of 0.5 mm, although other wire diameters are contemplated. In some embodiments, the diameter of the wire may be less than 3 mm, 2 mm, or 1 mm. In some embodiments, the diameter of the wire may be greater than 0.05 mm, 0.1 mm, 0.2 mm, 0.5 mm, or 1 mm. In some embodiments, the length of the spring arm may be less than 30 mm, 20 mm, or 10 mm. In some embodiments, the length of the spring arm may be greater than 1 mm, 5 mm, 10 mm, or 20 mm. In some embodiments, a spring may have an arm length of 10 mm. In some embodiments, a spring may have a coil diameter of 2 mm. In some embodiments, a spring may include fewer than 5, 3, or 2 coils. In some embodiments, a spring may include more than 1, 2, or 3. In some embodiments, a spring may include 2.5 coils. Of course, other suitable materials, geometries, and dimensions, including dimensions both greater and less than those noted above, are possible as the disclosure is not limited in this regard.

Figure 2D:
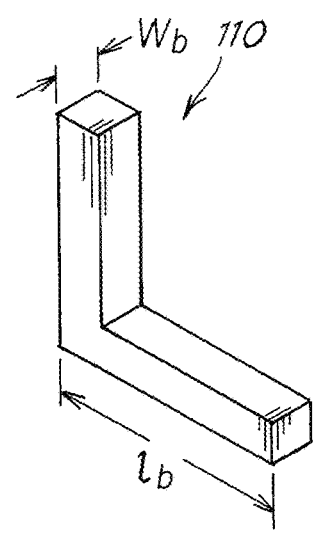
FIG. 2D depicts one embodiment of a beam of a reconfigurable medical device.

FIG. 2D depicts one embodiment of a beam 110. In some embodiments, a beam may be made of an elastic material, such as a thermoplastic polyurethane (e.g., Elastollan® 1185A). In some embodiments, the beam may be L-shaped. For example, in an embodiment of a reconfigurable medical device 100 with four arms 106 surrounding a central core 104, four L-shaped elastic beams 110 may couple each of the arms to two other adjacent arms. The beam may have a length $l_b$ and a width $w_b$. In some embodiments, the length of the beam may be less than 20 mm, 10 mm, or 5 mm. In some embodiments, the length of the beam may be greater than 1 mm, 2 mm, 5 mm, or 10 mm. In some embodiments, the length of the beam may be approximately 5 mm. In some embodiments, the width of the beam may be less than 3 mm, 2 mm, or 1 mm. In some embodiments, the width of the beam may be greater than 0.1 mm, 0.5 mm, 1 mm, or 2 mm. In some embodiments, the width of the beam may be approximately 1 mm. Of course, other suitable materials, geometries, and dimensions, including dimensions both greater and less than those noted above, are possible as the disclosure is not limited in this regard.

Figure 3:
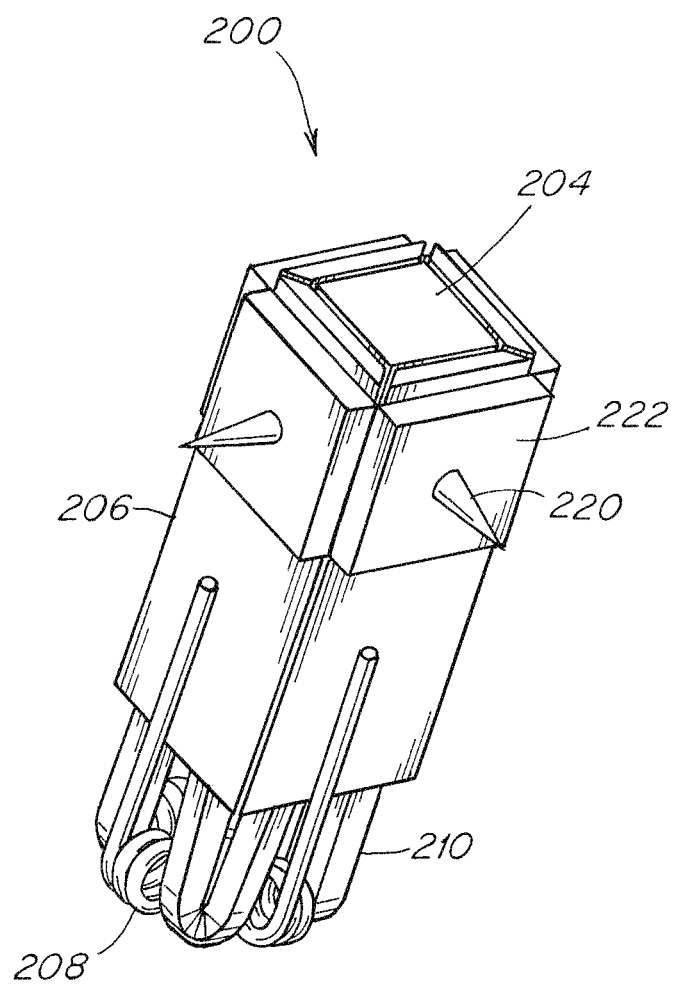
FIG. 3 depicts one embodiment of a reconfigurable medical device including drug-loaded needles on the deployable arms of the reconfigurable medical device.

FIG. 3 depicts one embodiment of a reconfigurable medical device 200 including drug-loaded needles 220. In the depicted embodiment, one or more needles may be coupled to corresponding distal portions of arms 206 that are located distally relative to proximal portions of the arms located proximate and connected to a corresponding portion of the core 204. A needle 220 may be coupled to an arm 206 through a needle base 222. The needle base may be coupled to the arm through adhesive, lock-and-key mechanical interlocking, welding, or any other suitable method of joining. However, in some embodiments, a needle 220 may be directly attached to an arm 206, without an intervening needle base 222. In some embodiments, a single arm 206 may include multiple needles 220. In some embodiments, only a subset of the arms 206 of a reconfigurable medical device 200 may include needles 220. In some embodiments, each needle 220 is the same, whereas in other embodiments one or more of the needles 220 may be different. For example, needles 220 of a reconfigurable medical device 200 may include multiple needs with different shapes and/or sizes. Additionally, needles 220 may be loaded with different therapeutic compounds. Fabrication of the needles is discussed in greater detail below with reference to FIG. 7.

Figure 4A:
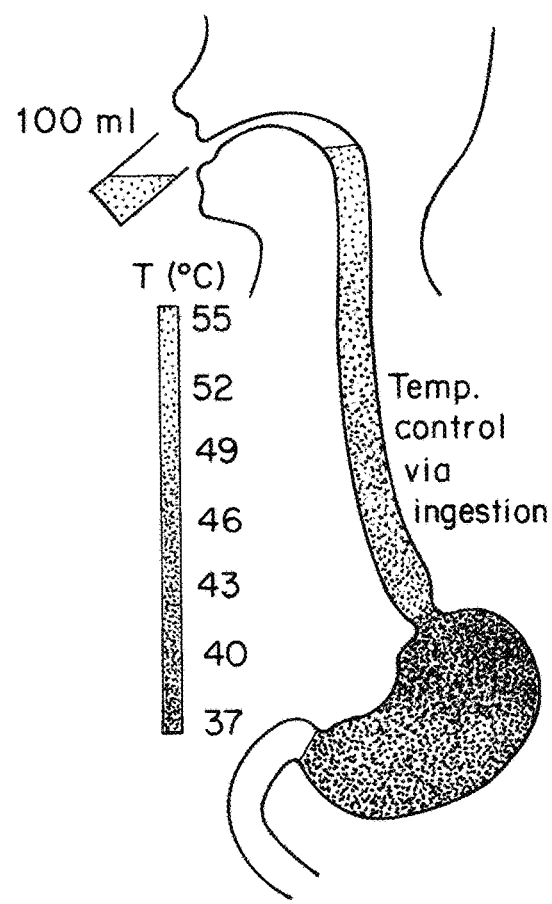
FIG. 4A depicts heat dissipation of an ingested liquid in the GI tract.

FIG. 4A depicts heat dissipation of an ingested liquid in the gastrointestinal tract. As shown in the figure, ingestion of 100 mL of 55° C. water may increase the temperature of the esophagus, but may have negligible effect on the temperature of the stomach. Additional details are provided below in the examples.

Figure 4B:
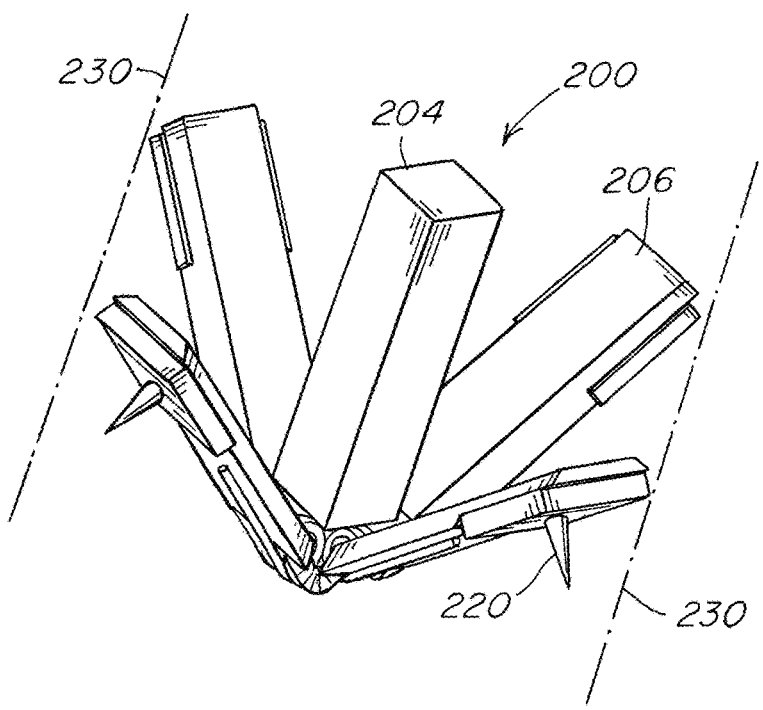
FIG. 4B depicts a reconfigurable medical device disposed within an esophagus in an expanded configuration.

FIG. 4B depicts a reconfigurable medical device disposed within an esophagus. As can be seen in the figure, the device 200 may not fully expand when deployed within the esophagus due to the expanded configuration of the device having a maximum transverse dimension, e.g. a diameter, that is larger than a transverse diameter of the esophagus of an average adult which may be between 18 mm and 20 mm. As such, when the device expands within an esophagus, the device may be constrained by the geometry of the walls 230 of the esophagus and only reach a partially expanded configuration (such as in FIG. 1B). Specifically, arms 206 of the device 200 may be prevented from fully expanding due to physical interaction with the walls 230 of the esophagus. Consequently, the arms may exert a force on the walls 230 of the esophagus. The force exerted by the arms may enable the needles 220 to engage with the tissue of the esophagus. Needles 220 may be configured such that the needles are able to penetrate the esophageal mucosa without perforation when device 200 is expanded within the esophagus. Needles 220 may be configured to retain the medical device in place within the esophagus when the needles engage with the walls 230 of the esophagus. In some embodiments, needles 220 may be configured to at least partially degrade after penetration into the esophageal wall, thereby releasing a therapeutic compound. The arms of the device may be subsequently retracted to reduce the diameter of the device, selectively enabling the device to pass through the esophagus and remainder of the GI tract.

A method of delivering a drug may include positioning a reconfigurable medical device contained in a capsule in a retracted configuration in an esophagus of a subject, dissolving the capsule, deploying a plurality of arms of the reconfigurable medical device using stored elastic energy to retain the reconfigurable medical device in the esophagus of the subject, and delivering the drug to tissue of the esophagus. The method may additionally include retracting the plurality of arms to reconfigure the reconfigurable medical device into the retracted configuration. The arms may be retracted by exposing the reconfigurable medical device to a temperature greater than a threshold temperature, such as by exposing the reconfigurable medical device to water ingested through a mouth of the subject. The threshold temperature may be a transition temperature of a shape memory spring, or other component, of the reconfigurable device.

Figure 5:
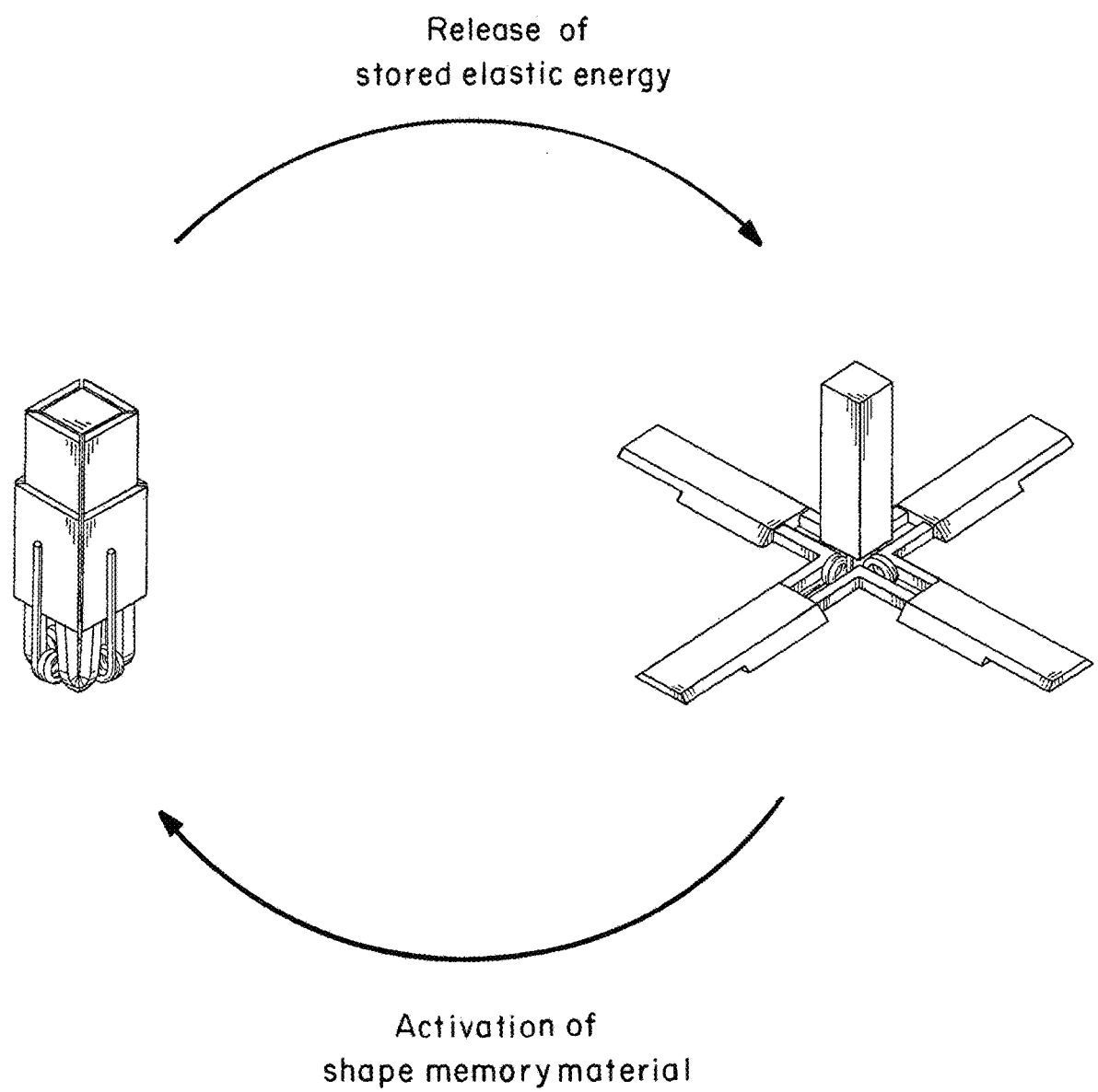
FIG. 5 depicts one embodiment of a reconfigurable medical device transitioning between retracted and expanded configurations.

FIG. 5 depicts one embodiment of a reconfigurable medical device transitioning between retracted and expanded configurations. In some embodiments, transition from a retracted configuration to an expanded configuration may include releasing stored elastic energy. In some embodiments, transition from an expanded configuration to a retracted configuration may include activating a shape memory material as described above.

In view of the above, in some instances, the various embodiments of a reconfigurable medical device described herein may have a maximum transverse dimension in the fully expanded configuration that is greater than 20 mm, 30 mm, and/or any other appropriate dimension. Correspondingly, the maximum transverse dimension of the device in the fully expanded configuration may be less than or equal to 50 mm, 40 mm, and/or any other appropriate dimension. Combinations of the foregoing are contemplated including, for example, a maximum transverse dimension of a device in the fully expanded configuration that is between or equal to 30 mm and 50 mm. Further, a maximum transverse dimension of the device in the fully retracted configuration may be selected to permit the device to pass through the esophagus, or other anatomical structure, of the subject. Accordingly, a maximum transverse dimension of the device in the retracted configuration may be less than or equal to 18 mm, 16 mm, 10 mm, and/or any other appropriate dimension. The maximum transverse dimension of the device in the retracted configuration may also be greater than or equal to 5 mm, 10 mm, and/or any other appropriate dimension. Thus, the maximum transverse dimension of the device in the retracted configuration may be between or equal to 5 mm and 18 mm. However, embodiments in which a device exhibits maximum transverse dimensions in the fully expanded and/or retracted configurations both greater and less than those noted above are also contemplated as the disclosure is not limited in this fashion.

In addition to the above, a longitudinal length of a device may have any desired dimension dependent on the particular application. However, in one embodiment, the length of a device may be greater than or equal to 10 mm, 20 mm, 30 mm, and/or any other appropriate dimension. Correspondingly, the length of a device may be less than or equal to 40 mm, 30 mm, 20 mm, and/or any other appropriate dimension. Combinations of the foregoing are contemplated including, for example, a length of a device that is between or equal to 10 mm and 40 mm. Of course device lengths both greater and less than those noted above are also contemplated as the disclosure is not so limited.

Figures 6A, 6B, 6C, 6D:
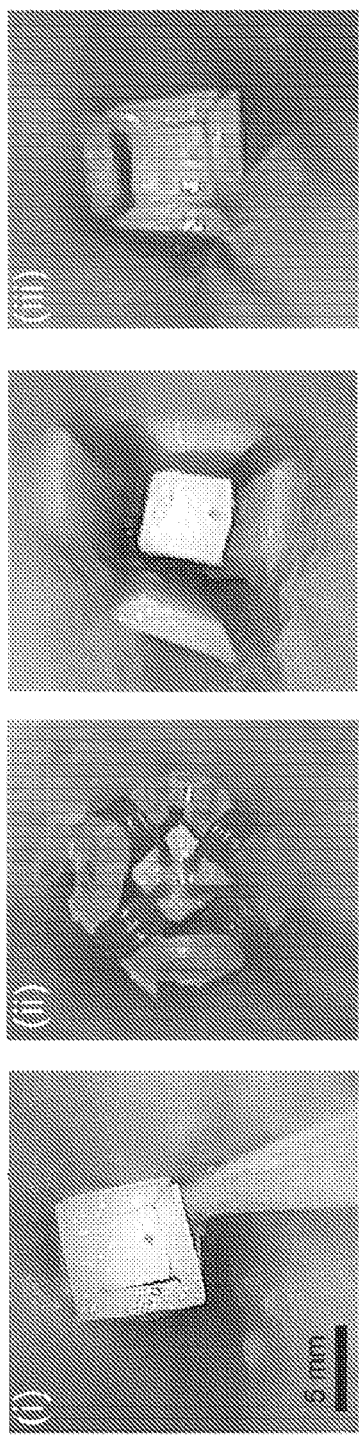
FIG. 6A depicts an in vivo endoscopic image of one embodiment of a reconfigurable medical device in a retracted configuration in an esophagus.
FIG. 6B depicts an in vivo endoscopic image of one embodiment of a reconfigurable medical device in a reverse configuration in an esophagus.
FIG. 6C an in vivo endoscopic image of one embodiment of a reconfigurable medical device in a direct configuration in an esophagus.
FIG. 6D an in vivo endoscopic image of one embodiment of a reconfigurable medical device again in a retracted configuration in an esophagus after administration of warm water.

FIGS. 6A-6D depicts in vivo endoscopic images of one embodiment of a reconfigurable medical device in different configurations in an esophagus. FIG. 6A shows the reconfigurable medical device in a retracted configuration. FIGS. 6B and 6C show the device deployed in reverse (FIG. 6B) and direct (FIG. 6C) directions. FIG. 6D shows the device again retracted after administration of 100 mL of 55° C. water. For additional details, see the examples below.

Figure 7A:
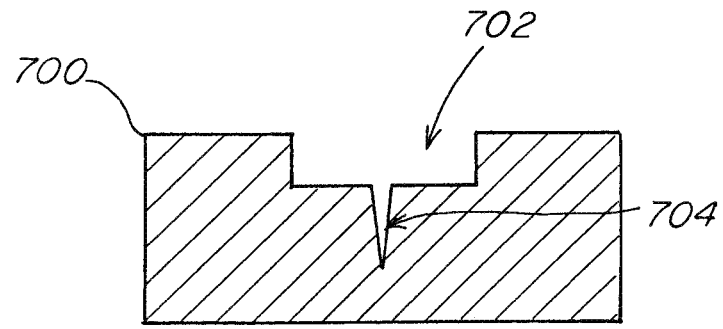
FIG. 7A depicts a schematic of one embodiment of a mold used to fabricate a needle.

FIGS. 7A-7D show one embodiment of a fabrication method for forming needles for use with the disclosed devices. FIG. 7A depicts a schematic of one embodiment of a mold 700 used to fabricate a needle. In some embodiments, the mold may be a negative formed from a positive needle geometry. For example, a positive needle geometry may be fabricated using a metal 3D printer. The negative mold 700 may be cast from the prototype needle using silicone rubber, latex, polyurethane, epoxy, plaster, or any other suitable molding and/or casting material. In some embodiments, the mold 700 may be 3D printed, or may be formed in a machining process. The mold 700 may include a first cavity 702, corresponding to a needle base, and a second cavity 704 extending away from the first cavity, corresponding to the needle itself. In some embodiments, needles may have geometries different than those shown in the figure, as the disclosure is limited to any particular cross sections shape or overall geometry of the needles. Additionally, although the mold shown in the figure may only accommodate a single needle, this is by example only, as the disclosure is not limited in regard to the number of needles that may be fabricated in a molding process. For example, a first cavity 702 may have multiple second cavities 704 to accommodate the formation of multiple needles.

Figure 7B:
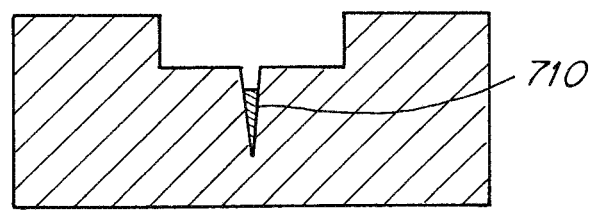
FIG. 7B depicts a therapeutic compound deposited into the mold shown in FIG. 7A.

FIG. 7B depicts a therapeutic compound 710 deposited into the mold shown in FIG. 7A. A therapeutic compound 710 may be pipetted into the second cavity 704 of the mold 700. In some embodiments, the therapeutic compound 710 may comprise small molecules including anti-inflammatories, such as steroids. In some embodiments, a steroid may be budesonide. In some embodiments, the therapeutic compound 710 may comprise monoclonal antibodies, such as infliximab or anti-IL-13. Of course, other therapeutic compounds may be loaded into the tip of a needle, and the disclosure is not limited with regard to the type of therapeutic compound. Therapeutic compounds may be of any suitable concentration or volume. Therapeutic compounds may be mixed or otherwise combined to form needles and/or needle bases comprised of multiple materials.

Figure 7C:
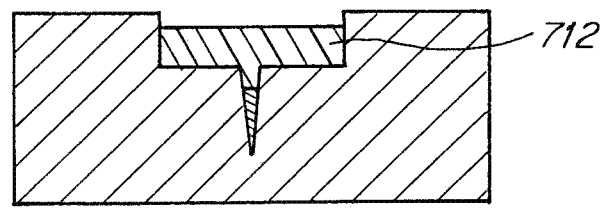
FIG. 7C depicts a polymeric solution deposited into the mold shown in FIG. 7A.

FIG. 7C depicts a polymeric solution 712 deposited into the mold shown in FIG. 7A. A sufficient amount of polymeric solution may be added so as to completely fill the second cavity 704 and partially fill the first cavity 702. In some embodiments, enough polymeric solution 712 may be added to overflow the first cavity 702. In some embodiments, the polymeric solution may include Soluplus and ethanol, poly(lactic-co-glycolic acid) (PLGA), polyvinylpyrrolidone (PVP), polylactic acid (PLA), carbohydrate, sugar glass, or any other suitable material that can be shaped into a needle and withstand insertion into esophageal mucosa. In some embodiments, a distinct polymeric solution may not be used, and a needle may be fabricated entirely from a therapeutic compound 710 depending on the properties of the specific therapeutic compound. In some embodiments, the polymeric solution 712 may be mixed with another material to aid in imaging. For example, Texas Red labeled dextran may be mixed with a polymeric solution to enable fluorescence imaging. Of course, other suitable materials may be mixed with a polymeric solution to enable other suitable types of imaging, as the disclosure is not limited in this regard.

Figure 7D:
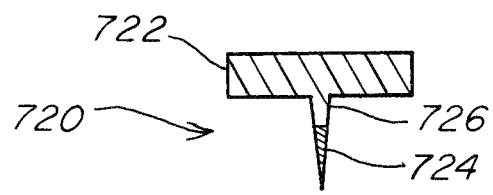
FIG. 7D depicts a needle loaded with a therapeutic compound formed from the mold shown in FIG. 7A.

After a therapeutic compound 710 and/or polymeric solution 712 are added to the mold 700, the molds may be placed in an evaporation system to spin cast. The needles may then be demolded from the mold 700, yielding a needle 720 attached to a needle base 722. The needle 720 and/or needle base 722 may be sanded, trimmed, or otherwise post-processed to modify the final geometry and/or remove unwanted features. FIG. 7D depicts a needle loaded with a therapeutic compound formed from the mold shown in FIG. 7A. The needle 720 may include a drug-loaded tip 724 as well as a non-drug region 726. In some embodiments, the entirety of the needle 720 may be drug-loaded, in which case the non-drug region 726 would not be present. In other embodiments, no drug may be included, in which the tip of the needle would not be drug-loaded. Additionally, while a specific manufacturing method has been illustrating in the figures for forming needles, it should be understood that any appropriate method of forming drug loaded needles appropriate for use in the disclosed systems may be used as the disclosure is not limited in this fashion.

Needles 720 may have any suitable shape, size, and/or aspect ratio. For example, needles with square, triangular, circular, ovular, rectangular, or any other appropriate cross-section may be used. Further, in some embodiments, a needle may have a variable cross section. For example, a diameter of the needle may decrease along the length of the needle. Additionally, depending on the embodiment, a needle may have a linear or non-linear profile as the disclosure is not limited to any particular shape of needle. In some embodiments, a length of a needle may be greater than 0.1 mm, 0.5 mm, 1 mm, 2 mm, 5 mm, or any other appropriate length. Correspondingly, a length of a needle may be less than 6 mm, 5 mm, 2 mm, or 1 mm. In some embodiments, a length of a needle may be between 4 mm and 6 mm. In some embodiments, a length of a needle may be approximately 5 mm. In some embodiments, a diameter of a needle may be at least 1 mm at its largest point, such as where the needle 720 intersects the needle base 722. In some embodiments, a maximum transverse dimension (e.g. a diameter) of a needle may be greater than 0.1 mm, 0.25 mm, 0.5 mm, 1 mm, 2 mm, or any other appropriate dimension. Correspondingly, a maximum transverse dimension of a needle may be less than 3 mm, 2 mm, 1 mm, 0.5 mm, or any other appropriate dimension. Of course, other needle lengths and transverse dimensions may be appropriate, including dimensions both greater and less than those noted above, as the disclosure is not limited in this regard.

Figure 8:
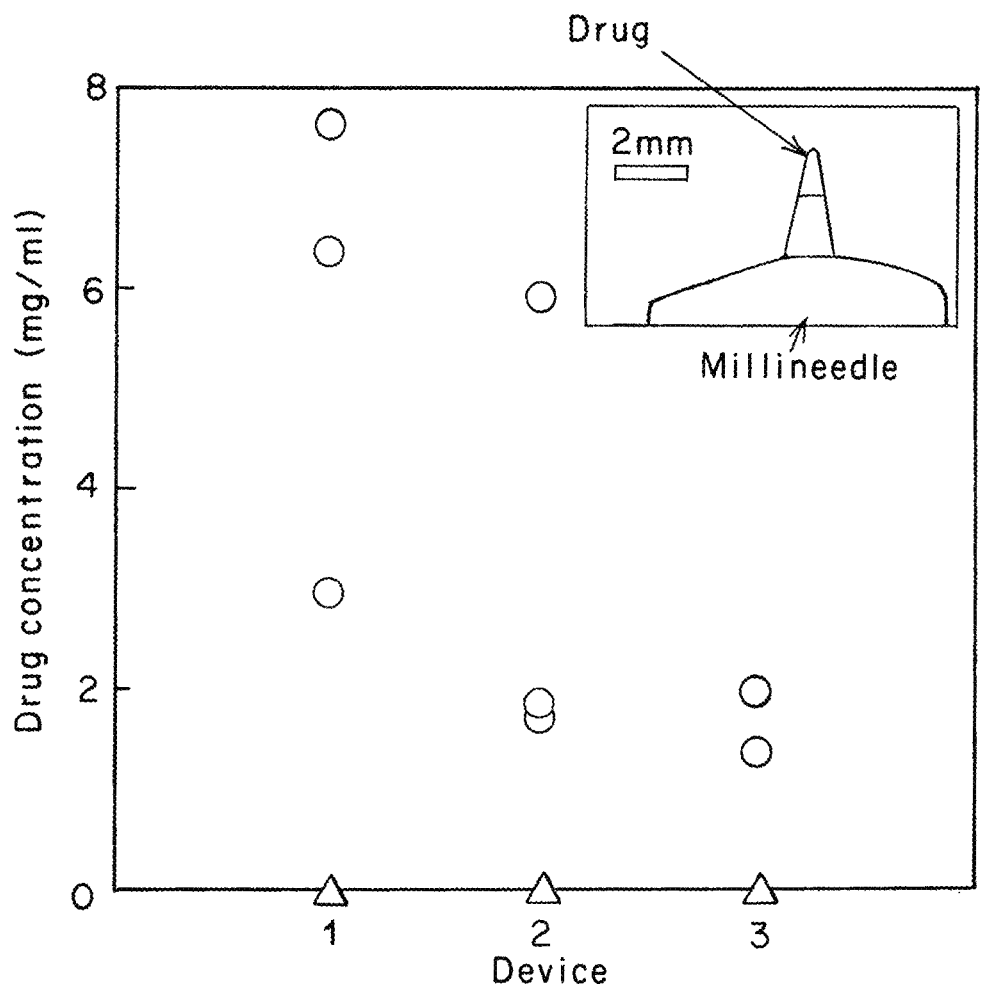
FIG. 8 depicts the concentration of drug delivered to the esophageal tissue for three different prototypes of an embodiment of a reconfigurable medical device.

FIG. 8 depicts the concentration of drug delivered to the esophageal tissue for three different prototypes of an embodiment of a reconfigurable medical device. Control needles without drug are shown as triangles, and the drug-loaded needles are shown as circles. The inset shows a needle loaded with 0.1 mg of drug at the tip. In some embodiments, the drug may be budesonide, although other suitable drugs or other therapeutic compounds are contemplated. For additional details, see the examples below.

Example: In Vivo Temperature Testing

A temperature measurement setup was fabricated to monitor temperature changes in the GI tract during the administration of a warm liquid. The setup was composed of an array of 16 bead wire type K thermocouple probes (model number: TP8735M available from Extech) attached together using waterproof Vinyl tape (part number: 190T available from 3M) with 5 cm spacing between each thermocouple. The thermocouple probes had a wide operating temperature range from −30 to 300° C. with accuracy of ±1° C. and 5 m long bead wire, enabling precise temperature measurement in narrow orifices of the digestive system such as the esophagus. The temperature data were recorded using a data logger (4 channel K-type thermometer with SD card data, model number 88598 available from AZ Instruments) with resolution 0.1° C., allowing real time monitoring of the luminal temperature. A total of four 4-channel data loggers were used to record data from 16 thermocouple probes. The setup was initially evaluated in vitro by inserting it into a 40 cm length Tygon tubing with an inner diameter approximately equivalent to the inner diameter of the esophagus (~18 mm). Temperatures were recorded following administration of water at different volumetric flowrates and input temperatures.

All animal experiments were conducted in accordance with protocols approved by the Committee on Animal Care at the Massachusetts Institute of Technology. The temperature in the esophagus and stomach during administration of warm water was measured in a large-animal model (three female 50-70 kg Yorkshire pigs). The pig was chosen as a model because its gastric anatomy is similar to that of humans and has been widely used in the evaluation of biomedical GI devices. Following overnight fasting, the animals were sedated with Telazol (tiletamine/zolazepam, 5 mg/kg IM), xylazine (2 mg/kg IM), and atropine (0.04 mg/kg IM) followed by endotracheal intubation and maintenance anesthesia with inhaled isoflurane (1-3% in oxygen). An endoscopic overtube (US Endoscopy) was placed into the esophagus under endoscopic visual guidance during esophageal intubation. Next, the temperature setup, made of an array of 16 thermocouple probes, was inserted through the overtube into the esophagus and stomach, and the overtube was then removed. When the correct placement was confirmed by radiographs (i.e., the position of all the probes was matched across all the experiments), the overtube was withdrawn such that the distal tip was at the proximal esophagus. Then, the pigs were secured in the seated position (i.e., vertical orientation) to mimic the orientation of the human GI tract while drinking.

A range of volumes of 55° C. warm water, V=10, 20, 50, 100, 200, 250 mL, were administered over 10 second periods (i.e., steady-state flowrate) and the temperature was recorded using the data loggers for all the probes. Upon administrating 100 mL of 55° C. water, the temperature rose considerably from the body temperature (i.e., ~35° C.) to 47-49° C., which is lower than the 55° C. ingested water due to heat dissipation in the esophagus. Each measurement was repeated 3 times in 3 different pigs with 2 minutes intervals between the tests to ensure the body temperature recovered to its initial value (i.e., 35 to 37° C.) before beginning a new test. For the high volumes of input water, V=100, 200, 250 mL, the water in the stomach was evacuated using vacuum suction after every measurement. The pouring period was 10 seconds for all the volumes except for V=10 and 20 mL, where the entire volume of water was poured quickly to mimic a single gulp. Finally, the change in the upper gastrointestinal tract temperature (ΔT) was calculated. ΔT is defined as $\Delta T = T_i - T_{Body}$ where $T_i$ denotes the temperature measured by the probe number i, i=1, 2, . . . , 16 and $T_{Body}$ denotes the body temperature, which varies between 35 to 37° C.

Example: In Vivo Temperature Testing—Data Interpretations

Temperature changes across the upper GI tract were characterized using thermocouple probes upon administration of various volumes of warm water (55° C.) administered at different rates to pigs in the seated position to mimic the orientation of the human GI tract while drinking. FIG. 4A shows an example of temperature distribution achieved in the upper GI tract upon ingestion of 100 mL of 55° C. water during a 10 second administration period (steady-state flowrate). The temperature rose notably to about 50° C. in the upper-esophagus, 48° C. in the middle-esophagus, and 45° C. in the lower-esophagus. However, no temperature change was detected in the stomach, indicating complete dissipation of heat over the length of the esophagus. The change in upper GI tract temperature (ΔT) was then recorded for increasing volumes of water at 55° C. The data suggested that temperature may be controlled in the esophagus and in the proximal stomach using high volumes of warm water (100, 200, 250 mL). Note that for the low volumes of warm water (10, 20 mL)—which is in the range of a single gulp—minimal temperature changes were recorded, supporting the notion that accidental actuation of thermoresponsive components through daily consumption of hot beverages may be unlikely. The temperature change in the bulk of the stomach appeared negligible regardless of the volume ingested. Thus, two zones with differential responses to warm liquids were established: esophageal and ex-esophageal. In summary, two temperature-triggerable zones in the GI tract were identified: the esophagus, which is responsive to ingestible warm liquid, and the gastric cavity (ex-esophagus), which can withstand ingestion of warm liquid.

Example: Flower-Like Prototype Manufacturing

The flower-like prototype is a multi-material design manufactured from three materials: (i) a thermoplastic polyester, poly(ε-caprolactone) (PCL) (molecular weight—40 kDa, Capa™ 6400 available from Perstorp), used for the arms and central core, (ii) a thermoplastic polyurethane, Elastollan® 1185A (available from BASF), used for the L-beam shaped elastic recoil component, and (iii) shape-memory Nitinol (NiTi) with a nominal transition temperature of 50° C. for torsion springs (available from Nexmetal Inc.).

Two aluminum molds were fabricated using a CNC mill (Othermill Pro, Bantam Tools) to cast the PCL arms and Elastollan® 1185A recoil components (L-beam shaped) via a two-step compression molding process. First, Elastollan® 1185A pellets were melted in the L-beam mold in an oven at 250° C. for 10 minutes. After compression and demolding, the flash was removed from the newly cast L-beams using a razor blade. Second, the L-beams were placed in the arm mold and PCL pellets were melted using a heat gun at 175° C. (sufficient to melt PCL but not Elastollan® 1185A). The L-beam recoil components and PCL were compressed using a weight that forced the PCL around the ends of the components and created a robust junction. A silicone rubber mold (Elite Double 32 available from Zhermack SpA) was used to cast the PCL central core. First, the core was fabricated using a 3D printer (Objet30 Pro, Stratasys) with VeroBlue (product number: RGD840, Objet) plastic material. Then the negative mold was cast using the silicone. Finally, the PCL core was cast by melting PCL pellets in the silicone mold using a heat gun at 175° C. followed by compression molding. After demolding and removing the flash, four 10 mm deep holes were drilled into the bottom of the core using a 0.60 mm drill bit. The holes were located at the midpoints of each edge of the bottom face's square cross-section. Finally, to assemble the prototype, one end of each torsional spring was glued to the outside of each arm using a cyanoacrylate based adhesive. After drying, adhesive was brushed onto the other ends of the Nitinol torsion springs, which were finally inserted into the corresponding holes in the core. The final dimensions of the flower-inspired prototype were in part chosen so that the prototype could be fitted into a 000-capsule. The resulting structure is similar to that shown in FIGS. 1A-1C.

Example: Transition Temperature of Shape Memory Material

To enable reconfiguration of the device, the relationship between the force exerted by the elastic beams (or other suitable structures configured to bias the arms away from the central core) and the force exerted by the shape memory springs (or other suitable structures configured to bias the arms toward the central core). It may be desirable for the springs to exert a force less than the force exerted by the beams in one state, and for the springs to exert a force greater than the force exerted by the beams in another state. These two states may correspond to temperature ranges relative to the transition temperature of the shape memory material:

$$F_{cr}^{Nitinol}(\text{at } T<T_c) < F_{cr}^{Elastollan} < F_{cr}^{Nitinol}(\text{at } T \geq T_c), \quad (1)$$

where $F_{cr}^{Nitinol}$ and $F_{cr}^{Elastollan}$ are the shape memory spring and elastic beam recoiling forces as a function of the temperature T, respectively, and $T_c$ is the nominal transition temperature of the shape memory material. A reconfigurable medical device that satisfies this relationship may exhibit robust expansion due to the elasticity of the beams at temperatures below the transition temperature ($T<T_c$) as well as robust retraction (folding) in response to thermal triggering of the shape memory springs at temperatures above the transition temperature ($T \geq T_c$).

The relationship expressed in Eq. (1) may be realized through selection of spring design parameters. Without wishing to be bound by theory, the spring recoiling force may be a function of spring wire diameter, spring arm length, spring coil diameter, and/or the number of coils in the spring, as well as other parameters. Considering a constant spring wire diameter and arm-length, coil diameter and number of coils represent a two-dimensional design that may be explored through systematic experimentation.

In some embodiments, the transition temperature of the shape memory springs may be selected with consideration of typical body temperature (approximately 35° C.-37° C.) and the temperature of an ingested liquid (e.g., 55° C.). In some embodiments, the transition temperature $T_c$ of the shape memory springs may be 50° C. In other embodiments, the transition temperature may be less than or greater than 50° C., based on parameters such as spring geometry and material, and based on desired system parameters, such as the temperature and/or volume of liquid ingested to trigger the thermo-responsive materials.

Example: Nitinol Heat Treatment

The shape-memory Nitinol was set using a fixture designed to hold it in the shape of the desired torsion spring inside a high temperature laboratory oven (LHT 6/30, Carbolite Gero). The fixed Nitinol wire was placed inside the preheated oven at 500° C. for 20 minutes and quenched in a room temperature water bath. The ends of the torsion spring were cut down to 10 mm each using a wire cutter. This procedure limits the maximum dimension of the spring to no more than 20 mm, yielding a device sufficiently small to pass through the pylorus.

Example: Flower-Like Prototype Mechanical Characterization

Performance characteristics of the prototype were evaluated. Specifically, the recoiling forces of the elastic recoil components and shape memory Nitinol springs, denoted by $F_{cr}^{Elastollan}$ and $F_{cr}^{Nitinol}$ respectively, were experimentally measured.

To measure the elastic recoiling force, $F_{cr}^{Elastollan}$, the prototype was fixed to the bottom of a uniaxial testing machine (Instron 5942 series Universal Testing System) with a 10 N load cell. In this configuration, three of four arms were folded and one arm was free to move. The free arm was then pushed directly down by the tester until fully folded. The peak load was recorded as the recoiling force, which may be the same as the force exerted from each arm upon expansion of the prototype. For the selected dimensions of the Elastollan® L-beam recoil component, a force of $F_{cr}^{Elastollan}=0.4$ N was recorded.

To measure the spring recoiling force, $F_{cr}^{Nitinol}$ in response to a temperature change, a 50 N force gauge (FG-3005, Shimpo Instruments) with a hook attachment was clamped in a retort stand. One arm of each of multiple Nitinol springs with nominal transition temperature $T_c=50°$ C. and variable coil numbers and diameters was fixed and the other arm interfaced snugly with the hook. Warm water at 50° C. was poured onto each spring with differing numbers of coils and coil diameters, and the peak load recorded by the force gauge was recorded as the spring recoiling force.

Example: Degradable Polymeric Millineedle Manufacturing

The millineedles were fabricated from a mixture of Soluplus® (BASF) and ethanol (EtOH), with the addition of 70 kDa dextran labeled with Texas Red™ (Thermo Fisher Scientific) or budesonide (available from Carbosynth) at different points in the fabrication process.

To manufacture the polymeric degradable needles, a molding approach was used. First, negative silicone molds were fabricated by casting a silicone rubber (Elite Double 32 available from Zhermack SpA) using a custom metal 3D printed needle (printed by Proto Labs). Then, the needles were cast into the silicone molds using a (1:1 by weight) polymeric mixture of ethanol and Soluplus®. For X-ray visualization, 15% weight ratio of $BaSO_4$ was added to the polymeric mixture. The reconfigurable medical device with mounted polymeric millineedles on the outer side of the arms was designed to penetrate the esophageal mucosa without perforation.

To enable fluorescence imaging, Texas Red™ labeled dextran was loaded into the millineedles. To prepare these millineedles, a 25 mg/mL solution of Texas Red™-labeled dextran in EtOH was prepared, and then 20 μL of this solution was added to the Soluplus/EtOH mixture. The mixture was mixed using a DAC 150.1 FVZ-K SpeedMixer (FlackTek Inc.) for 5 minutes at approximately 3000 RPM to create a homogenous solution. The silicone molds were filled with the polymeric solution.

To make millineedles loaded with budesonide, 1 µL of a 100 mg/mL suspension of budesonide in EtOH was pipetted into the tips of the silicone molds prior to pouring the polymeric solution, ensuring to mix the suspension during pipetting. This procedure resulted in 0.1 mg of budesonide loaded at the tips of needles. The molds were then placed in an evaporation system (Genevac DD-4X) to spin cast at room temperature and left for three days for the EtOH to evaporate completely. The millineedles were then demolded and the substrates were sanded down to a thickness of approximately 1 mm and trimmed down to fit on the tips of the flower-like prototype's arms using a razor blade. The millineedles were finally mounted to the arms using a cyanoacrylate based adhesive.

Example: Ex Vivo Testing of Flower-Like Prototype—Macromolecule Delivery

The flower-like prototype with three needles loaded with dextran labeled with Texas Red and one control needle was deployed in the esophagus harvested from a Yorkshire pig 10 minutes after euthanasia. The esophagus was rinsed for approximately 10 seconds under running tap water to wash away contaminants such as gastric fluid. To deploy the prototype, a custom 3D printed fixture was used. The fixture consisted of a 10 mm square tube 3D printed (Formlabs, Form 2) out of Grey plastic (product number: RS-F2-GPGR-04, Formlabs) and a 20 mm diameter tube 3D printed (Objet30 Pro, Stratasys) out of VeroClear plastic (product number: RGD810, Objet). The 20 mm tube was placed inside the ex vivo esophagus to hold it open for deployment, and the prototype was placed inside the square tube. The prototype and the square tube were then inserted into the esophagus via the 20 mm tube. Once the prototype reached the mid-esophagus, the prototype was pushed out of the square tube using a long rod to deploy. After deployment, the prototype was left in place for 20 minutes before retrieval. The Texas red deposition was assessed using an IVIS® Spectrum in vivo imaging system (PerkinElmer) at fluorescent excitation and emission filter set of 570 nm and 620 nm, respectively.

Additionally, histological analysis was performed on tissue biopsies to characterize the depth of penetration. Biopsies were taken at the penetration sites, where needles coated with green tissue marking dye (product number: 0736-3 available from Cancer Diagnostics, Inc.) penetrated. The biopsies were fixed in formalin fixative (Sigma Aldrich) for 24 hours and were transferred to 70% ethanol. Tissue samples were then embedded in paraffin, cut into 5 µm-thick tissue sections, and imaged using an Aperio AT2 Slide Scanner (Leica Biosystems, Buffalo Grove, IL).

Example: Ex Vivo Testing of Flower-Like Prototype—Small Molecule Delivery

Three flower-like prototypes each equipped with three needles loaded with 0.1 mg budesonide per needle and one control needle were deployed in the esophagi of three Yorkshire pigs, harvested 10 minutes after euthanasia. The needles were placed there for 20 minutes to degrade before retrieving the esophagus and taking 8 mm diameter biopsies at the four penetration sites. The biopsies were then frozen until extraction. Budesonide was extracted from the tissue by placing each biopsy in methanol and shaking overnight. The samples were centrifuged at 1500 g for 10 minutes, and a fraction of the supernatant was collected. These samples were evaporated to dryness, spiked with 200 µL of 250 ng/mL of hydrocortisone (internal standard) in acetonitrile to cause precipitation of any remaining proteins. Samples were vortexed and sonicated for 10 minutes and centrifuged for 10 minutes. Two hundred microliters of supernatant were pipetted into a 96-well plate containing 200 µL of nanopure water and used for UPLC-MS/MS analysis. (See FIG. 8.)

UPLC-MS/MS analysis was performed on a Waters® ACQUITY UPLC®-I-Class System aligned with a Waters® Xevo—TQ-S mass spectrometer (Waters Corp., Milford, MA). Liquid chromatographic separation was performed on an Acquity® UPLC Charged Surface Hybrid C18 (50 mm×2.1 mm, 1.7 µm particle size) column at 50° C. The mobile phase consisted of aqueous 0.1% formic acid, 10 mM ammonium formate solution (Mobile Phase A) and an acetonitrile: 10 mM ammonium formate, 0.1% formic acid solution (95:5 v/v) (Mobile Phase B). The mobile phase had a continuous flow rate of 0.6 mL/min using a time and solvent gradient composition. The initial composition (100% Mobile Phase A) was held for 1 minute, following which the composition was changed linearly to 50% Mobile Phase A over the next 0.25 minutes. At 1.5 minutes the composition was 20% Mobile Phase A and at 2.5 minutes the composition was 0% Mobile Phase A, which was held constant until 3 minutes. The composition returned to 100% Mobile Phase A at 3.25 minutes and was held at this composition until completion of the run, ending at 4 minutes, where it remained for column equilibration. The total run time was 4 minutes, and sample injection volume was 2.5 µL. The mass spectrometer was operated in the multiple reaction monitoring (MRM) mode. Sample introduction and ionization was by electrospray ionization (ESI) in the positive ionization mode. MassLynx® 4.1 software was used for data acquisition and analysis.

Stock solutions of budesonide and internal standard hydrocortisone were prepared in methanol at a concentration of 500 µg/mL. A twelve-point calibration curve was prepared in methanol ranging from 1-5000 ng/mL.

Example: In Vivo Testing of Flower-Like Prototype

Three female Yorkshire pigs weighing approximately 50-70 kg were used for in vivo evaluation. Following overnight fasting, the animals were sedated. An overtube (US Endoscopy), with endoscopic guidance, was placed into the proximal esophagus to assist the placement of the flower-like prototype while held in the retracted configuration by a single-use endoscopy snare (Captivator™ II, Boston Scientific). Upon releasing from its retracted configuration in the upper esophagus, due to elastic energy trapped in the elastic components during folding, the prototype rapidly deployed, enabling the contact of the four arms with the esophageal wall. Once in position, 100 mL of 55° C. water was administered via the overtube into the esophagus to thermally trigger the Nitinol springs, which increased the temperature in the esophagus by $\Delta T \sim 13°$ C. to reach the approximate transition temperature $T_c=50°$ C. of the springs. This process resulted in fully retracting the arms of the prototype. The prototype was then allowed to pass into the pig's stomach, where it was retrieved intact. The same experiment was performed with the prototype in the reverse direction. The details of deployment, closure and passage of the flower-like prototype for both direct and reverse directions were recorded. Following the above procedures, the animals were recovered and they were monitored clinically at least twice a day for any evidence of morbidity, including lethargy, inappetence, decreased fecal output or any other abnormal signs. (See FIG. 6.)

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

What is claimed is:

1. A reconfigurable medical device comprising:
a central core; and
a plurality of arms rotatably coupled to the central core such that the plurality of arms are configured to rotate outwards away from the central core to selectively reconfigure the reconfigurable device between a first retracted configuration and a second expanded configuration, wherein in an initial state each arm of the plurality of arms is biased outwards away from the central core into the second expanded configuration, wherein when the reconfigurable device is exposed to a temperature greater than a threshold temperature, each arm of the plurality of arms is biased towards the central core into the first retracted configuration, and wherein, in the first retracted configuration, a longitudinal axis of each arm of the plurality of arms is parallel to a longitudinal axis of the central core and, in the second expanded configuration, the longitudinal axis of each arm of the plurality of arms is perpendicular to the longitudinal axis of the central core.

2. The reconfigurable medical device of claim 1, further comprising a plurality of therapeutic compound-loaded needles coupled to distal portions of the plurality of arms.

3. The reconfigurable medical device of claim 1, wherein each arm of the plurality of arms is biased towards the central core by a shape memory component.

4. The reconfigurable medical device of claim 3, wherein each arm of the plurality of arms is connected to an elastic component that uses stored elastic energy to bias the reconfigurable medical device into the second expanded configuration.

5. The reconfigurable medical device of claim 3, wherein the shape memory component includes a shape memory spring.

6. The reconfigurable medical device of claim 3, wherein the shape memory component comprises one or more selected from the group of a shape memory alloy and a shape memory polymer.

7. The reconfigurable medical device of claim 1, further comprising a dissolvable capsule at least partially surrounding the central core and the plurality of arms, wherein the dissolvable capsule retains the plurality of arms in the first retracted configuration.

8. The reconfigurable medical device of claim 1, wherein the threshold temperature is greater than normothermia.

9. The reconfigurable medical device of claim 1, wherein a maximum transverse dimension of the reconfigurable medical device in the first retracted configuration is less than 18 mm.

10. The reconfigurable medical device of claim 1, wherein a maximum transverse dimension of the reconfigurable medical device in the second expanded configuration is greater than or equal to 20 mm and less than or equal to 40 mm.

11. The reconfigurable medical device of claim 1, wherein the reconfigurable medical device is configured to be deployed in an esophagus of a subject.

12. The reconfigurable medical device of claim 1, wherein each arm is configured to rotate about a respective rotational axis located outwardly from an outer perimeter of the central core.

* * * * *

UNITED STATES PATENT AND TRADEMARK OFFICE
CERTIFICATE OF CORRECTION

PATENT NO. : 12,303,659 B2
APPLICATION NO. : 17/293804
DATED : May 20, 2025
INVENTOR(S) : Robert S. Langer et al.

Page 1 of 1

It is certified that error appears in the above-identified patent and that said Letters Patent is hereby corrected as shown below:

In the Specification

At Column 1, Lines 17-20, Government License Rights:
"This invention was made with Government support under Grant No. R37 EB000244 awarded by the National Institutes of Health. The Government has certain rights in the invention."

Should be:
--This invention was made with government support under EB000244 awarded by the National Institutes of Health. The government has certain rights in the invention.--

Signed and Sealed this
Seventeenth Day of June, 2025

Coke Morgan Stewart
*Acting Director of the United States Patent and Trademark Office*